US010177421B2

(12) United States Patent
Saunders et al.

(10) Patent No.: US 10,177,421 B2
(45) Date of Patent: *Jan. 8, 2019

(54) BATTERY CELL STRUCTURE WITH LIMITED CELL PENETRATIONS

(71) Applicant: Battelle Memorial Institute, Columbus, OH (US)

(72) Inventors: James H. Saunders, Worthington, OH (US); Steven M. Risser, Reynoldsburg, OH (US); C. Alexander Morrow, Gahanna, OH (US)

(73) Assignee: Battelle Memorial Institute, Columbus, OH (US)

( * ) Notice: Subject to any disclaimer, the term of this patent is extended or adjusted under 35 U.S.C. 154(b) by 195 days.

This patent is subject to a terminal disclaimer.

(21) Appl. No.: 14/620,635

(22) Filed: Feb. 12, 2015

(65) Prior Publication Data

US 2016/0240897 A1 Aug. 18, 2016

(51) Int. Cl.
*H01M 10/48* (2006.01)
*G01N 21/95* (2006.01)
(Continued)

(52) U.S. Cl.
CPC ............ *H01M 10/48* (2013.01); *G01N 21/59* (2013.01); *G01N 21/84* (2013.01); *G01N 21/95* (2013.01);
(Continued)

(58) Field of Classification Search
CPC combination set(s) only.
See application file for complete search history.

(56) References Cited

U.S. PATENT DOCUMENTS

| 5,949,219 A | 9/1999 | Weiss | |
|---|---|---|---|
| 2001/0019794 A1* | 9/2001 | Horie | H01M 10/488 429/90 |

(Continued)

FOREIGN PATENT DOCUMENTS

| JP | 2000215870 A | 8/2000 |
|---|---|---|
| JP | 2003344020 A | 12/2003 |
| WO | WO 2014/026093 A1 * | 2/2014 |

OTHER PUBLICATIONS

Hintermaier, Frank; International Search Report and Written Opinion; International Application No. PCT/US2013/054302; dated Oct. 30, 2015; The International Bureau of WIPO, Geneva, Switzerland.

(Continued)

*Primary Examiner* — Kaity V Chandler
(74) *Attorney, Agent, or Firm* — Stevens & Showalter, LLP (57) ABSTRACT

Light is transmitted from a light source through or from a separator of a battery cell and received by one or more light detectors. The light that is normally transmitted through the separator is scattered, absorbed, wavelength-shifted or otherwise distorted by an impending fault in the vicinity of or within the separator. The change in light due to the impending fault is measured by a detector and a signal from the detector is processed to identify the impending fault so that a warning can be generated indicative of the impending fault. In particular, one or both of the light source and detector are enclosed within a battery cell housing and receive power from the electrodes of the battery cell.

20 Claims, 9 Drawing Sheets

(51) Int. Cl.
*G01N 21/59* (2006.01)
*H01M 10/0525* (2010.01)
*G01N 21/84* (2006.01)

(52) U.S. Cl.
CPC .... *H01M 10/0525* (2013.01); *H01M 2220/10* (2013.01); *H01M 2220/20* (2013.01); *Y02E 60/122* (2013.01)

(56) References Cited

U.S. PATENT DOCUMENTS

| | | | |
|---|---|---|---|
| 2005/0210672 A1* | 9/2005 | Reynolds | G02F 1/155 29/830 |
| 2006/0102455 A1 | 5/2006 | Chiang et al. | |
| 2006/0170410 A1 | 8/2006 | Bjorn | |
| 2009/0099799 A1 | 4/2009 | Barsoukov et al. | |
| 2009/0123826 A1 | 5/2009 | Nitzan et al. | |
| 2009/0246620 A1 | 10/2009 | Lee et al. | |
| 2010/0124250 A1 | 5/2010 | Lachenmeier et al. | |
| 2010/0175235 A1 | 7/2010 | Nielsen et al. | |
| 2011/0054561 A1 | 3/2011 | Visco et al. | |
| 2011/0148359 A1 | 6/2011 | Noguchi | |
| 2011/0200863 A1 | 8/2011 | Xiao et al. | |
| 2011/0236735 A1 | 9/2011 | Fuse | |
| 2012/0070713 A1 | 3/2012 | Whear et al. | |
| 2012/0070714 A1 | 3/2012 | Chambers et al. | |
| 2012/0070747 A1 | 3/2012 | Whear et al. | |
| 2012/0106593 A1 | 5/2012 | Zhou et al. | |
| 2012/0115008 A1 | 5/2012 | Sano et al. | |
| 2012/0115036 A1 | 5/2012 | Lee et al. | |
| 2012/0148880 A1 | 6/2012 | Schaefer et al. | |
| 2012/0188086 A1 | 7/2012 | Xie et al. | |
| 2012/0249154 A1 | 10/2012 | Dao et al. | |
| 2013/0216867 A1 | 8/2013 | Schaefer et al. | |
| 2015/0155605 A1 | 6/2015 | Dvorsky et al. | |
| 2016/0013522 A1 | 1/2016 | Morrow et al. | |

OTHER PUBLICATIONS

Related U.S. Appl. No. 14/620,568; entitled "Optical Waveguide Methods for Detecting Internal Faults in Operating Batteries;" filed Feb. 12, 2015 by James H. Saunders et al.

Related U.S. Appl. No. 14/620,600; entitled: Integral Light Sources and Detectors for an Optical Sensor to Detect Battery Faults; filed Feb. 12, 2015 by C. Alexander Morrow et al.

Wu, Hui et al.; "Improving Battery Safety by Early Detection of Internal Shorting with a Bifunctional Separator"; Oct. 13, 2014; Nature Communications.

Communication pursuant to Rules 161(1) and 162 EPC; European Patent Application No. 13750468.4; dated Mar. 26, 2015; European Patent Office; Munich, Germany.

Jianhua Han; First Office Action; Chinese Patent Application No. 201380042586.1; dated Jul. 5, 2016; State Intellectual Property Office of the People's Republic of China.

Frank Hintermaier; Notice of Intention to Grant; EPC Application No. 13750468.4; dated Mar. 17, 2016; European Patent Office; Munich, Germany.

Bui, Dung Y.; Non-final Office Action; U.S. Appl. No. 14/620,600; dated Sep. 23, 2016; United States Patent and Trademark Office; Alexandria, Virginia.

Bui, Dung V.; Non-final Office Action; U.S. Appl. No. 14/414,984; dated Oct. 11, 2016; United States Patent and Trademark Office; Alexandria, Virginia.

Williams, Arun C.; Notice of Allowance; U.S. Appl. No. 14/620,568; dated Oct. 12, 2016; United States Patent and Trademark Office; Alexandria, Virginia.

Williams, Arun C.; Supplemental Notice of Allowability; U.S. Appl. No. 14/620,568; dated Oct. 20, 2016; United States Patent and Trademark Office; Alexandria, Virginia.

Bui, Dung V.; Final Office Action; U.S. Appl. No. 14/620,600; dated May 3, 2017; United States Patent and Trademark Office; Alexandria, VA.

Bui, Dung V.; Final Office Action; U.S. Appl. No. 14/414,984; dated May 30, 2017; United States Patent and Trademark Office; Alexandria, VA.

Bui, Dung V.; Non-Final Office Action; U.S. Appl. No. 14/620,600; dated Oct. 27, 2017; United States Patent and Trademark Office; Alexandria, VA.

Bui, Dung V.; Final Office Action; U.S. Appl. No. 14/620,600; dated May 25, 2018; United States Patent and Trademark Office; Alexandria, Virginia.

Bui, Dung V.; Office Action; U.S. Appl. No. 14/414,984; dated Apr. 30, 2018; United States Patent and Trademark Office; Alexandria, Virginia.

Bui, Dung V.; Notice of Allowance; U.S. Appl. No. 14/620,600; dated Oct. 3, 2018; United States Patent and Trademark Office; Alexandria, Virginia.

* cited by examiner

BATTERY CELL STRUCTURE WITH LIMITED CELL PENETRATIONS

GOVERNMENT LICENSE RIGHTS

Aspects of this invention were made with support from the United States (US) Government under Contract No. DE-AR0000272 awarded by the Advanced Research Projects Agency-Energy (ARPA-E). The US Government may have certain rights in the invention.

RELATED PATENT APPLICATIONS

The present application is related to two concurrently-filed patent applications: U.S. application Ser. No. 14/620,600, entitled INTEGRAL LIGHT SOURCES AND DETECTORS FOR AN OPTICAL SENSOR TO DETECT BATTERY FAULTS), and U.S. application Ser. No. 14/620,568, entitled OPTICAL WAVEGUIDE METHODS FOR DETECTING INTERNAL FAULTS IN OPERATING BATTERIES, the disclosures of which are incorporated herein by reference in their entirety.

BACKGROUND OF THE INVENTION

The present invention relates in general to batteries and, more particularly to methods and apparatus for periodic, if not continuous, monitoring of the development of impending faults in secondary or re-chargeable batteries at the cell level using optical signals during operation of the batteries in applications such as electric vehicles and electrical grid storage.

SUMMARY OF THE INVENTION

One aspect of embodiments of the present invention relates to a battery structure for monitoring development of impending faults of a battery cell in which the battery structure includes a cell housing and a battery cell separator, located within the cell housing, formed of a light transmitting material that has light transmission characteristics that are a function of a state of impending faults of the battery cell. The structure also includes a first electrode on a first side of the battery cell separator; a second electrode on a second side of the battery cell separator; a light source, located within the cell housing, for transmitting light into said battery cell separator; and a light detector, located within the housing, for receiving light transmitted through the battery cell separator. Thus, a fault state of a portion of the battery cell associated with the light detector can be determined based on the received light.

Another aspect of embodiments of the present invention relates to a method for monitoring development of impending faults of a battery cell in a battery structure, the battery structure comprising a battery cell housing which encloses first and second electrodes on opposite sides of a battery cell separator, the battery cell separator formed of a light transmitting material that has light transmission characteristics that are a function of a state of impending faults of the battery cell. In particular, the method includes transmitting, from a light source located within the battery cell housing, light into said battery cell separator; receiving, at a light detector located within the battery cell housing, light transmitted through the battery cell separator; and determining a fault state of a portion of the battery cell associated with the light detector based on the received light.

DETAILED DESCRIPTION OF THE INVENTION

The present application describes some aspects of battery technology also described, at least in part, in U.S. patent application Ser. No. 14/414,984, entitled OPTICAL MONITORING OF BATTERY HEALTH, filed Jan. 15, 2015, which claims priority to PCT Patent Application No. PCT/US2013/054302, entitled OPTICAL MONITORING OF BATTERY HEALTH, filed Aug. 9, 2013, which claims the benefit of U.S. Patent Application Ser. No. 61/681,669, entitled OPTICAL MONITORING OF BATTERY HEALTH, filed Aug. 10, 2012, the disclosures of which are incorporated herein by reference in their entirety.

State-of-the-art secondary or re-chargeable batteries, particularly those based on lithium chemistries, provide some of the highest energy densities of any electrical energy storage devices currently commercially available. Their performance has led to their widespread usage in mobile electronic devices and electric vehicles with ever increasing periods of energy availability and/or size reduction as improvements are made to the battery composition and geometry. However, along with these advantages, these batteries have also exhibited catastrophic failures that have hampered some developments, especially those associated with electric vehicles. Manufacturers of re-chargeable batteries have incorporated several ways of providing margins of safety to their devices, but it has been shown that in some cases these countermeasures are not enough. Moreover, as compositions or constructions of these batteries are modified to improve safety, their energy density often is compromised. In fact, some experts believe that commercially available assemblies may exhibit only twenty percent (20%) of the energy density and performance that is theoretically achievable in order to provide products having high margins of safety.

Several techniques, such as Electrochemical Impedance Spectroscopy (EIS), have been developed to measure degradation of lithium ion and other re-chargeable batteries. These techniques provide significant insight to the condition of individual cells of a battery pack and are often employed in research efforts. Unfortunately, most of these techniques cannot be applied to the battery in situ and certainly are not amenable to periodic if not continuous monitoring of battery fault development throughout its operating cycles and life. In fact, the operation of the battery must be interrupted to employ these diagnostic techniques, and they are too cumbersome and expensive to be considered for use on each fielded battery pack.

In accordance with the teachings of the present application, a completely different approach is taken to battery fault monitoring based on optical measurement techniques. Fundamentally, electrical performance of the battery and its associated load or charging provisions does not interfere with optical signals. Also, optical components do not interfere with the battery's operation so that continuous sensing through all phases of battery charging and discharging is possible. Using optical components that are similar in physical size to the components of a battery allows for monitoring structures to be built into or integrated with the battery cell design without significantly impacting its geometry. The teachings of the present application apply to single cell batteries and multiple cell batteries and can be used in batteries for portable electronic devices, off-grid applications, electric vehicles and the storage of electricity on the electrical grid, where the latter two applications may have hundreds or thousands of cells. The teachings of the present application are generic and should be applicable to a wide variety of battery chemistries and types.

Figure 1:
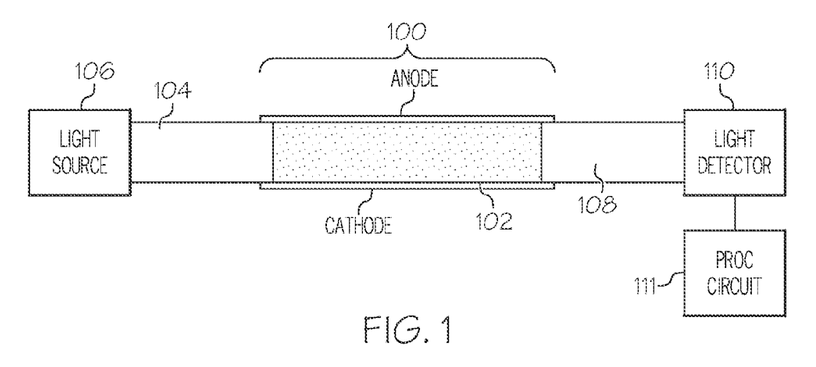
FIG. 1 schematically illustrates a battery cell separator in accordance with the teachings of the present application having a light transmitting optical fiber and a light receiving optical fiber integrated into the battery cell for monitoring the fault state of the battery cell.

A first embodiment of a battery cell 100 made in accordance with the teachings of the present application is shown in FIG. 1 wherein an edge of the battery cell 100 is shown. The battery cell 100 includes a battery cell separator 102 with electrolyte, which is a standard component placed between the electrodes, anodes and cathodes, of battery cells. The separator 102 with electrolyte has light transmission characteristics that are a function of the state of impending faults of the battery cell 100. Light is transmitted into the separator 102 via a first optical fiber 104 from a light source 106 coupled to the first optical fiber 104. In accordance with the teachings of the present application, there may be one or more light sources such as light emitting diodes, semiconductor diodes, lasers, lamps and the like. In the embodiment of FIG. 1, light is transmitted through the separator 102 and received via a second optical fiber 108 by a light detector 110 coupled to the second optical fiber 108. The light detector 110 is sensitive to the wavelengths of interest which will depend on the specific structure and chemistry of the battery cell.

The detector 110 may be any conventional light detector, such as photodiodes, phototransistors or more exotic detectors currently or to become available in the future. Since the light transmission characteristics of the separator 102 with electrolyte is a characteristic of the fault state of the battery cell 100, the fault state of the battery cell 100 can be determined by a processing circuit 111 that processes the output signal from the detector 110 to estimate whether an incipient fault is present in the battery cell 100. The processing circuit 111 may also process the output signal from the detector 110 to determine a temperature profile along the battery cell 100, the chemical species along the battery cell 100, the internal pressure within the battery cell 100 and the like.

Figure 2:
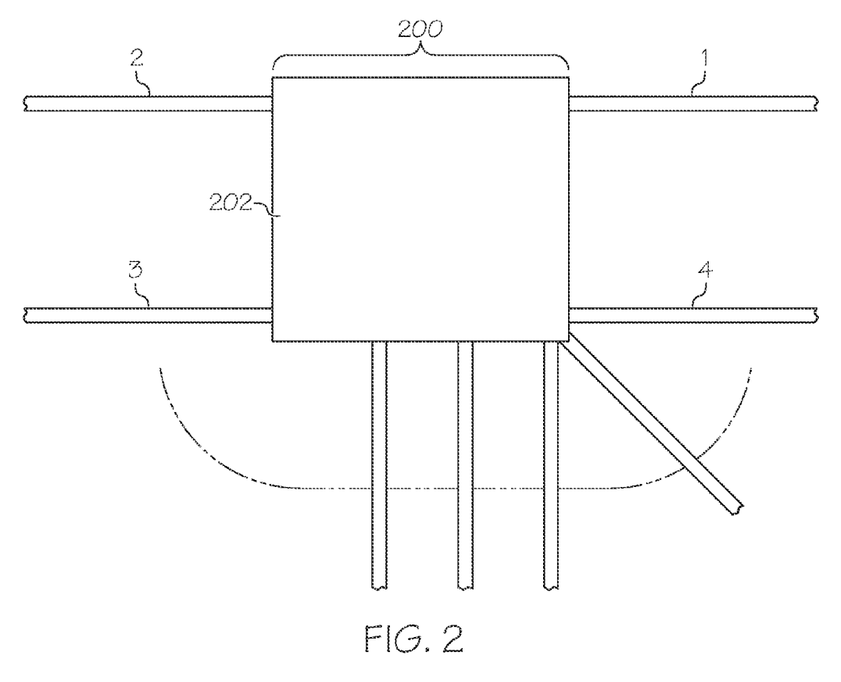
FIG. 2 schematically illustrates a battery cell separator in accordance with the teachings of the present application having light transmitting and/or light receiving optical fibers integrated into a plurality of locations around the battery cell for monitoring the fault state of the battery cell.

The thickness of battery cell separators is often tens of microns, and the optical fibers ideally have a similar or slightly smaller diameter. As described above with reference to FIG. 1, light can be sent from one fiber, such as the first fiber 104, and received by the other fiber, such as the second fiber 108. Alternately, one or both of the optical fibers 104, 108 may sense optical emissions generated within the separator 102 if the light source 106 is replaced by a light detector. Moreover, multiple fibers may be arranged around the periphery of a battery cell, as shown in FIG. 2, to optimize parameter detection and even yield detection of localized faults within the cell. In FIG. 2, a face of a battery cell 200 is shown with optical fibers 1 through n being coupled to a separator 202 of the battery cell 200 at various locations around the periphery of the battery cell 200. Light sources and light detectors can be coupled to the optical fibers 1 through n as required for given monitoring applications.

Figure 3:
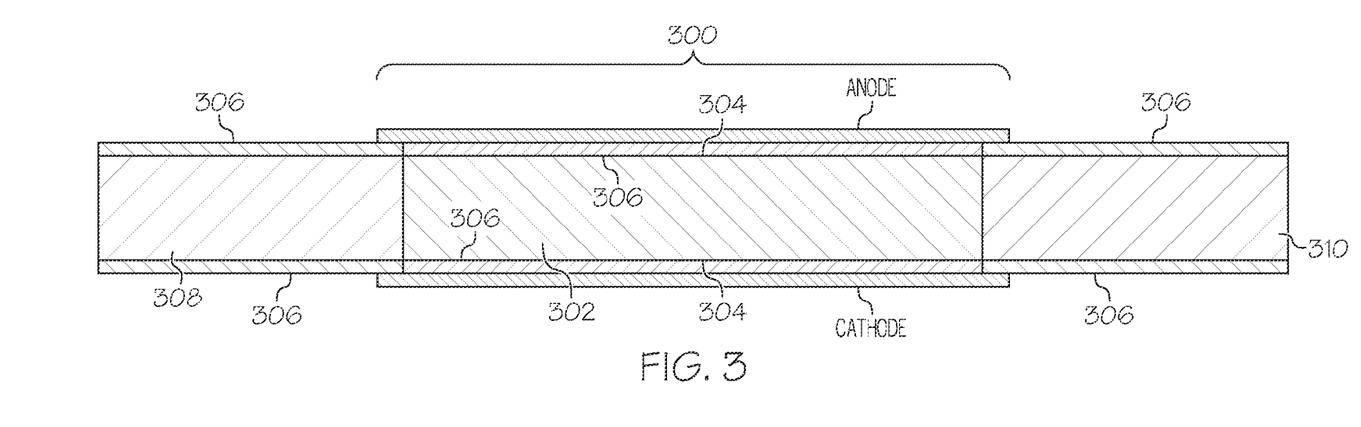
FIG. 3 schematically illustrates a battery cell separator in accordance with the teachings of the present application having a light transmitting optical fiber and a light receiving optical fiber integrated into the battery cell for monitoring the fault state of the battery cell wherein the separator includes waveguide characteristics.

The optical characteristics of a battery cell 300 can be improved by using a layered separator 302 such as that shown in FIG. 3. Like optical fibers themselves, the outer layers 304 of the separator 302 are similar to the inner core of the separator 302, but have a refractive index lower than that of the core of the separator 302. There are several known methods to cause this lower refractive index, such as use of slightly different polymer compositions, functionalization or halogenations of the inner core or outer layers, changes in polymer processing, among others. As shown in FIG. 3, the optical performance of the separator 302 can be improved by forming a layer 306 of material over the outer face surfaces 304 of the separator 302. The outer face surfaces 304 may also be formed over optical fibers 308, 310 coupled to the separator 302. Such separators may be formed by laminating layers of material together to yield light waveguide characteristics for the separators, or the separators may be treated to reduce the refractive index only at their face surfaces.

One preferred class of materials for separators is polyolefin, such as polyethylene (PE). PE is also used in optical fibers, and cladding is created by fluorinating the surface of the fibers. A similar technique may be applied to the separator to give it improved optical wave guiding characteristics. Alternatively, a material such as polypropylene (PP), which has lower refractive index than PE, may be laminated to each of the face surfaces of the PE layer to create a separator having optical waveguide characteristics.

Many battery separators are known to have a highly porous morphology. These pores can act to scatter light, leading to poor optical transmission through the separator. One method to reduce this optical scattering is to use light with longer wavelengths, which will scatter less from the pores. A second approach is to use an electrolyte in the battery which has refractive index similar to that of the separator. Many of the electrolytes examined more recently in the literature, such as ionic liquids, have refractive index approaching or exceeding that of many common battery separator polymers.

In any event, light from the source(s) enters an associated separator where it may be scattered, absorbed or otherwise distorted by an impending fault condition in the vicinity or within the separator. The fault condition could be a physical embodiment, such as a dendrite, or could be the presence of chemical species associated with the degradation of the separator, electrolyte, binder or other components of the battery cell, or a change in temperature or electric field due to the fault condition. The change in light is measured by the detector and the processing circuit converts that electrical signal to an appropriate signal for warning of an impending fault within the system.

An alternate arrangement for a battery cell is to use an ion-conducting polymer electrolyte membrane in place of the separator 102 plus electrolyte of FIG. 1. The polymer electrolyte membrane can be made transparent and homogeneous, and may offer optical advantages over using a separator membrane plus electrolyte. The refractive index of the outer surfaces of the polymer electrolyte membrane can then be altered to enhance wave guiding, or multiple, different polymers can be laminated to form a polymer electrolyte membrane with improved light wave guiding characteristics.

Figure 4:
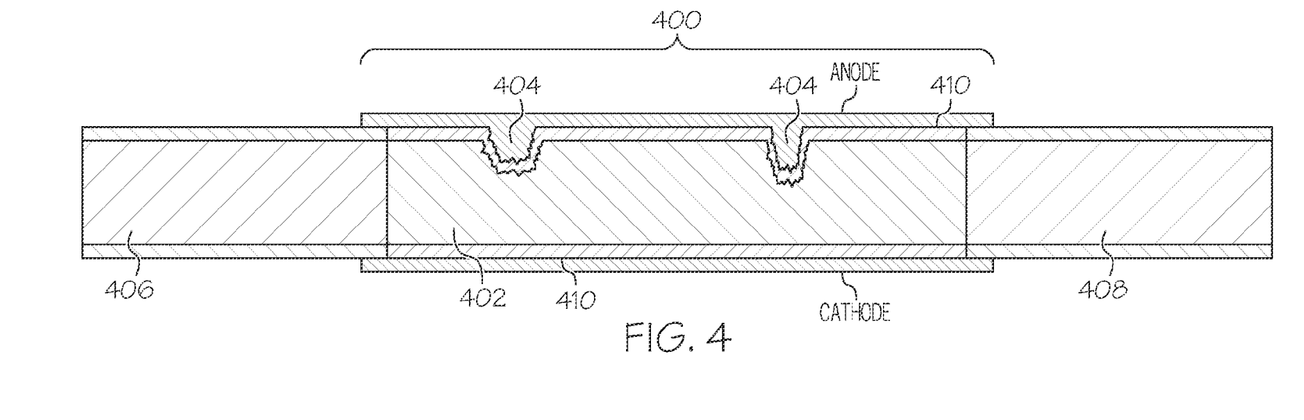
FIG. 4 schematically illustrates a Lithium Ion battery cell separator in accordance with the teachings of the present application having a light transmitting optical fiber and a light receiving optical fiber integrated into the battery cell for monitoring the fault state of the battery cell and showing the growth of Lithium into the separator.

One of the principal modes of lithium ion battery failure is shorting due to dendritic growth of lithium metal on an electrode surface of a cell 400 having a separator 402, as shown in FIG. 4. Mechanisms leading to the growth of dendrites 404 are the subject of many current research programs. However, it is generally known that if the dendrites cascade through the separator 402 and form a short circuit with the opposing electrode, large currents can flow and subsequently intense heat is generated. The heat readily impacts the rest of the battery cell and neighboring battery cells, setting off a chain reaction. In the extreme, the entire battery overheats and can burst into flames.

Accordingly, detecting the presence of metallic dendrites, such as the dendrites 404, imposing on the separator 402, is an important aspect of the battery cells of the present application. As depicted in FIG. 4, the dendrites 404 either distort the separator 402 or puncture into it, and these perturbations of or intrusions into a separator having waveguide characteristics can be detected using optical techniques. The transmission of light from one optical fiber, such as optical fiber 406, through the separator 402 to another optical fiber, such as the optical fiber 408, will be diminished and significant disturbances to the cladding 410 of the separator 402 will yield disproportionally greater impacts to the transmission of light. Improved sensitivity and localization of significant dendrites may be attained by employing multiple sensing fibers around the periphery of a separator, for example as shown by the separator 202 of FIG. 2.

Other optical effects are also envisioned for the battery cells of the present application. For example, the formation of dendrites will create localized "hot spots" as the current density increases at the dendrite and resistive heating ensues. Elevated temperatures within the separator should change the index of refraction in that area or portion of the battery cell, creating a change of input-to-output signal characteristics of the separator. In addition, localized heating will create an infrared (IR) signature that is different from the rest of the cell, even if the entire cell is experiencing elevated temperature due to current flow. The IR wavelengths may be passively detected by one or more optical fibers associated with the separator of the battery cell as described above.

By further manipulation of either the separator or optical fiber composition or both, other battery fault conditions can be monitored. For example, materials designed to react to the presence of electric fields could provide an early detection of dendrite formation. Since an electric potential is present across the separator and the microscopic features of the dendrite distort and accentuate the electric field at the tip of the growing dendrite, materials designed to sense and optically respond to these fields would produce a unique response from optical detectors associated with battery cells in accordance with the teachings of the present application.

As is known, not all battery degradations are due to dendritic formations. Over time, electrolyte chemistry can also change, and the formation of new compounds within a battery cell should be detectable using other optical measurements, such as changes in the IR absorption spectra of the separator in the battery cell. For example, according to research conducted at the University of Michigan, gases may be formed at electrode-to-separator boundaries with such gas formation leading to increased pressure within a battery cell. These same gases could react with engineered separators and optical fibers to yield readily detectable optical signatures indicative of the gas presence. In addition, as thermal runaway is initiated, the electrolyte breaks down into other compounds, which could similarly be detected optically. Other degradations in electrode or electrolyte may be detected similarly. Reactions may produce luminescence or the fiber configuration could support spectroscopic measurement techniques.

An alternate method to sense thermal runaway could be achieved by creating a wave guiding separator using materials where the inner wave guiding layer changes refractive index differently from the outer layers. In most polymers, the refractive index decreases with increasing temperature, but the rate of this decrease varies from polymer to polymer. If the refractive index of the wave guiding layer or layers decreases more rapidly than that of the outer layers of the optical fiber, there will be a temperature at which the refractive indices are equal. As the temperature approaches this value, the wave guiding properties will be lost and the membrane will become more lossy. This increase in optical loss could be used as an indicator of excess temperature in the cell. By controlling the composition of the different layers it should be possible to tune the temperature where the lossy behavior begins to facilitate optical detection.

For example, two general classes of separators can be used in various embodiments of the invention of the present application. The first separator class is gelled polymer membranes, in which a solvent is used to gel a polymer. These gelled polymer membranes generally have good optical clarity, but commonly are thick (>200 microns) and may have low ionic conductivity. It is possible to sandwich these membranes between glass slides and then use a hot press to make the membranes sufficiently thin for use as battery separators without decreasing the optical clarity.

In a first example, an ionic liquid based sodium ion conducting gel polymer electrolyte was prepared as reported in Solid State Ionics 181 (2010) 416-423, which is incorporated herein by reference, by replacing the sodium triflate with lithium triflate. This membrane was placed onto a glass slide which had first been coated with a low refractive index polymer, for example a low index fluoropolymer such as EP-18, a 50/50 copolymer of hexafluorobutyl methacrylate and tetrafluoropropyl methacrylate, and then covered with a second glass slide which also had a low refractive index polymer coating. The membrane was then hot pressed at a temperature of 275° C. for ~1 hour to 100 μm with shims and left to cool to room temperature prior to releasing pressure.

Figure 5:
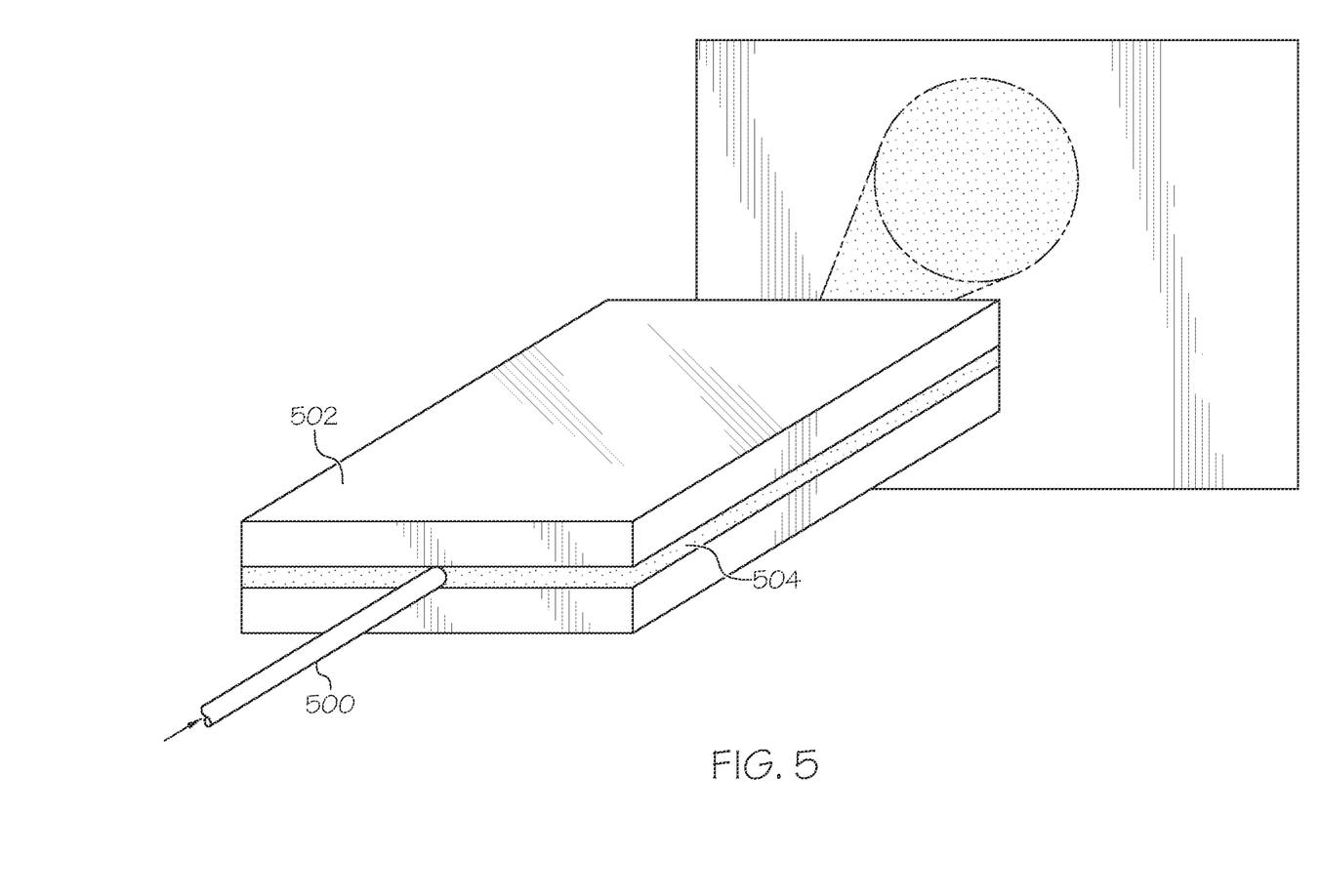
FIG. 5 schematically illustrates light guiding characteristics of a gelled polymer membrane sandwiched between two glass slides by butt-coupling and optical fiber to the membrane and inserting 633 nm light.
Figure 6:
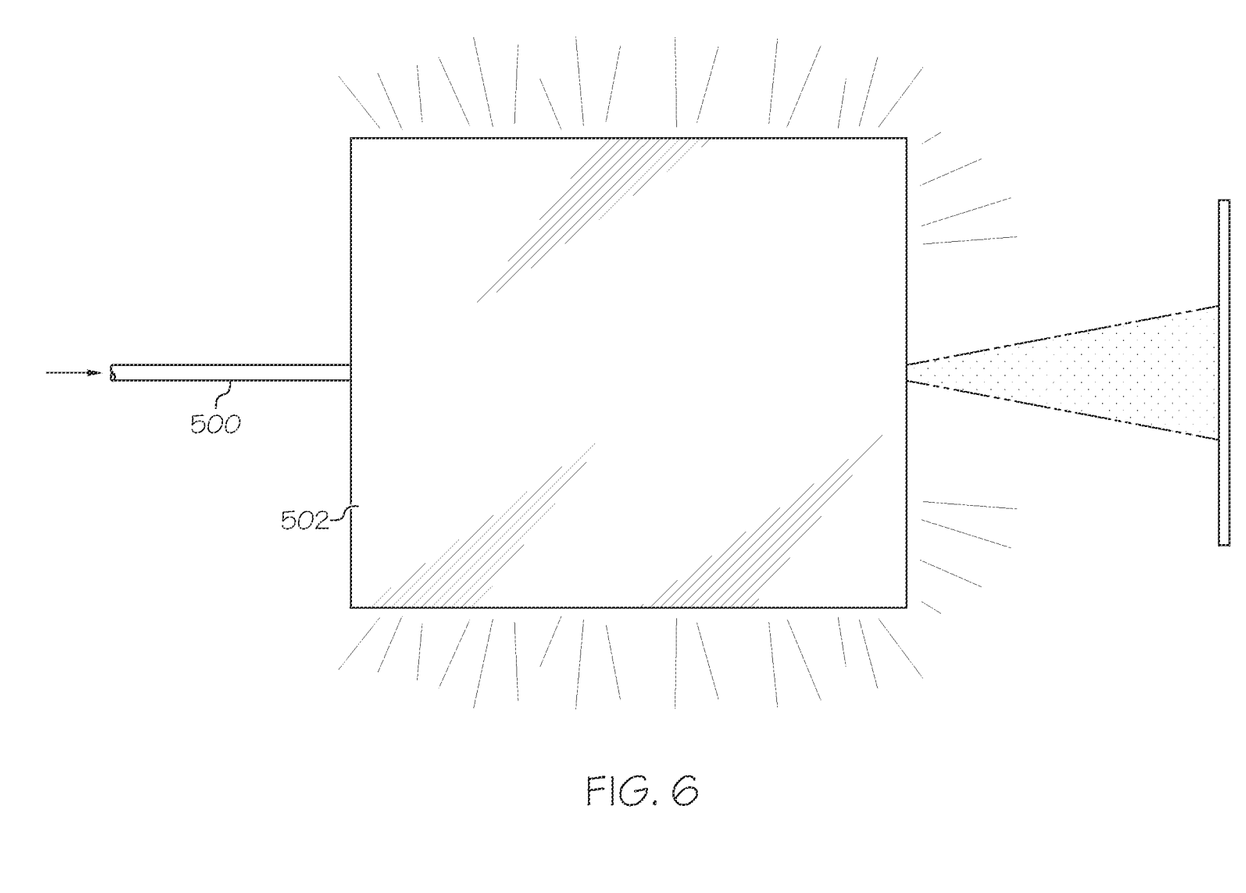
FIG. 6 schematically illustrates a side view of the membrane of FIG. 5 showing transmission of light throughout the membrane as indicated by the scatter light emitted from the side edge of the membrane.

The light guiding characteristics of the membrane were then examined by butt-coupling an optical fiber 500 to the sample 502 as shown in FIG. 5, and inserting visible 633 nm light into the fiber 500. When the fiber 500 was coupled to the membrane 504, light was scattered throughout the membrane, but a large fraction of light exited the far end of the membrane, as shown in FIG. 5. FIG. 6 is a top view of the sample 502 showing transmission of light through the sample 502 as well as scattering of light throughout the sample 502 illustrated by light exiting membrane via the sides of the sample 302.

A second separator class is a porous polyolefin separator, which consists of a thin (<35 micron) film of a polymer such as polyethylene or polypropylene which has been drawn to produce a highly porous membrane. When a thickness of the separator is below 35 microns, its impedance is beneficially reduced. While separators have been created as thin as 4 microns, they do not typically have the mechanical integrity needed to reliably perform as a separator. The size of the pores can be controlled by the drawing process, example pores can be below 100 nm in size with materials having pores of 25 nm or below being presently available as well. Beneficial results may occur when the material's pore size is less than ~½ the wavelength (or smaller) of the light being transmitted into the separator. Thus, in general, a smaller pore size is preferable for materials which match all the other criteria desirable for a separator.

The transmission, or scattering, of light through such a membrane is controlled by the scattering of light from the pores. The scattering of light from a single spherical scatterer can be calculated directly as is known in the industry (See, e.g., van de Hulst H., Light scattering by small particles, 1957, J. Wiley & Sons, NY.). In particular, light scattering from a single spherical particle is a function of the ratio of the refractive index of the electrolyte (particle) to that of the membrane (medium) and the number of particles in a box that measures 25 microns by 25 microns by 1 centimeter (cm). Such a box represents the region a light ray might trace in traveling through a 1 cm section of a separator. In the example below, the number of particles is representative of a membrane having porosity of 40%.

Thus, for a spherical scatterer 200 nm in diameter, if the refractive index of the membrane and electrolyte differ by 0.01, over 95% of the light would be transmitted and not scattered. Also, if the particle has a diameter of 100 nm, a refractive index difference of 0.04 would still correspond to more than a 91% transmission of light. These examples values are similar whether the ionic liquid refractive index is higher or lower than the membrane.

Table 2 below shows the scattering for needle-shaped particles, such as might represent pores through a thin-film membrane. In the case of needle-shaped particles, the scattering is larger than for the spherical particles, but it is still possible to achieve light transmission of over 90%.

TABLE 2

Scattering by needle-shaped particles.

| lambda (nm) | 1550 | 1550 | 1550 | 1550 |
| --- | --- | --- | --- | --- |
| diameter (nm) | 50 | 100 | 50 | 100 |
| Length (nm) | 25000 | 25000 | 25000 | 25000 |
| polymer index | 1.49 | 1.49 | 1.49 | 1.49 |
| electrolyte index | 1.48 | 1.48 | 1.485 | 1.485 |
| cross section (micron2) | 1.030E−06 | 1.649E−05 | 2.573E−07 | 4.117E−06 |
| number density for box 25 micron by 25 micron by 1 cm | 5.09E+07 | 1.27E+07 | 5.09E+07 | 1.27E+07 |
| BLOCKED AREA (micron^2) | 5.25E+01 | 2.10E+02 | 1.31E+01 | 5.24E+01 |
| BLOCKED AREA (%) | 8.40% | 33.59% | 2.10% | 8.39% |

There are several ionic liquids that satisfy the example refractive indices listed above while, as an example, the refractive index of the polymer in the membrane can be in the range of 1.49 to 1.51, depending on the film processing.

Table 3 below shows a list of some ionic liquids which have refractive indices in the range discussed above. The refractive index will change slightly upon addition of the salt, and will also change with the temperature of the ionic liquid.

TABLE 3

| ionic liquid | refractive index |
| --- | --- |
| 1-ethyl-3-methylimidazolium tosylate | 1.538 |
| 1-hexyl-3-methylimidazolium chloride | 1.515 |
| 1-methyl-3-octylimidazolium chloride | 1.505 |
| 1-ethylpyridinium ethylsulfate | 1.50252 |
| 1,3-dimethylimidazolium methyl sulfate | 1.4827 |
| 1-butyl-3-methylimidazolium 2-(2-methoxyethoxy)ethyl sulfate | 1.48 |
| 1-butyl-3-methylimidazolium methylsulfate | 1.47942 |
| 1-ethyl-3-methylimidazolium ethyl sulfate | 1.4794 |
| 1-butyl-3-methylimidazolium perchlorate | 1.4725 |
| 1-ethyl-3-methylimidazolium octyl sulfate | 1.471 |

The inventors conclude that by controlling the spatial variation in index of refraction due to pore size and other structures and materials to meet certain conditions related to the variation of index of refraction within the separator, even more light should be transmitted through the porous structures providing the structures meet certain conditions, i.e., the regularity of the spacing between the pores and the regularity of the size of the pores since the more randomness there is in either factor, the more scattering. More particularly, candidate polymers are likely to be transparent if the scale of the variations of index of refraction caused by mismatch between the pores and space between pores is less than one-half the wavelength of the transmitted light. Typically this can result in scattering that is an order of magnitude less than the calculation results obtained by assuming scattering by an array of independent single scatters. Also, matching the index of refraction between the polymer and ionic solution may also further reduce the scattering.

For example, with an assumed IR light source of 1500 nm, structural variations that are less than 750 nm or 0.75 microns will reduce light scattering effects. Consequently, separators with spatial variations of index of refraction less than one-half the wavelength of incident light, or separators with appropriate spatial variations that meet the criteria for transparency are candidates for the optical separator described in the present application. The structural variations in index of refraction can be due to the pore size, where the pores may contain the electrolyte, trapped gases or liquids or particles, or other materials. As long as these variations meet the criteria described herein, they may be considered as candidates for use in the invention of the present application. Other techniques described in the present application may be used in combination with this aspect of the invention of the present application.

Two general classes of separators that can be used in the invention of the present application have been mentioned above. In the first, gelled polymer separators, the electrolyte is used to gel the polymer resulting in separators with quasi-homogeneous structure but decreased ionic transport. In the second class of separators, conventional polyolefin separators are used with an ionic liquid electrolyte. The refractive index of the polyolefin is typically in the range 1.49 to 1.52, and the ionic liquid electrolyte is selected to have a closely matching refractive index to minimize scattering loss. In accordance with the teachings of the present application, there is an additional class of separator plus electrolyte pairing that can be used in the context of using a battery separator as an optical waveguide. The separator can be made from polyvinylidene fluoride (PVDF), which is commonly used to make separators. The refractive index of PVDF is about 1.42, varying to some degree dependent on processing, which is close to the refractive index of many common battery electrolytes such as propylene carbonate (RI=1.4189), vinyl ethylene carbonate (RI=1.45) or ethylene carbonate (RI=1.4158). A mixture of these carbonates can be formulated that closely matches the refractive index of the PVDF separator, particularly when the lithium salt is incorporated into the electrolyte.

Figure 7A:
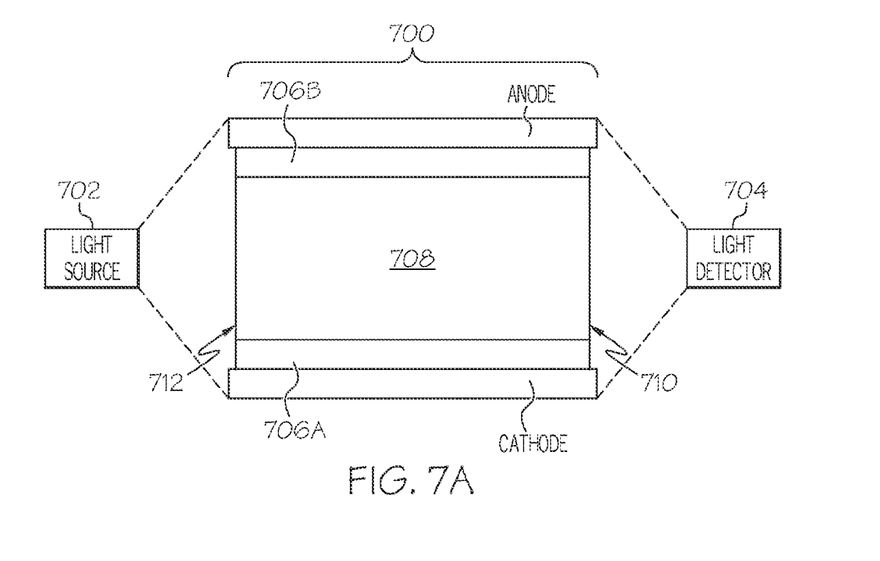
FIG. 7A schematically illustrates a battery cell having a waveguide separator in accordance with the principles of the present application.

FIG. 7A schematically illustrates a battery cell 700 having a waveguide separator in accordance with the principles of the present application. In particular, there is a light source 702 in optical communication with the cell 700 such that light from the light source 702 can be transmitted into the cell 700. There is also a light detector 704 that is in optical communication with the cell 700 such that it can receive light transmitted through the cell 700. As described earlier, the light is transmitted into the battery cell separator (706A, 706B, 708 of FIG. 7A) that is positioned between electrodes of the battery cell 700 such as between an anode and a cathode of the battery cell 700.

Although FIG. 7A shows a configuration with the light source 702 in optical communication with one edge 712 of the cell 700 and the light detector 704 in communication with a different edge 710 of the cell 700, other configurations of the light source 702 and light detector 704 are contemplated. For example, both the light source 702 and the light detector 704 may be in optical communication with the same edge (e.g., 712). In this configuration, light from the light source 702 that is scattered within the cell separator (706A, 706B, 708) so as to exit back out of the edge 712 would be detectable by the light detector 704.

The cell separator of FIG. 7A comprises a core section 708 and cladding sections 706A, 706B. An electrolyte is also present in between the anode and cathode of the cell 700. As discussed in examples described below, the cladding sections 706A, 706B may be constructed from a material different than the core section 708 or may be first and second voids between the core 708 and, respectively, the anode and cathode, with each such void filled with the electrolyte.

The separator (706A, 706B, 708) retains its properties that allow it to function as a battery separator but also includes properties that allow it to function as a waveguide, as described below. As such, the separator (706A, 706B, 708) allows ionic conduction through the electrolyte which is contained within the separator, either within pores of the separator (i.e., a porous core section 708 and/or porous cladding sections 706A, 706B when present) or within the separator material itself (e.g., an ion-conducting polymer electrolyte membrane). Also, to function as a waveguide, the separator is divided into two components: the core section 708 that transmits (or scatters) light and the cladding sections 706A, 706B on the outside of the core section 708 that confine a portion of the transmitted light in the core section 708 by total internal reflection.

In one example, having both a core material and a cladding material, a core material can be considered which is close in value to the index of refraction of an electrolyte contained within the pores of the core material (e.g., +/−0.01). The pores of the cladding material will also contain the electrolyte as well so that ions can conduct through the cladding sections 706A, 706B. However, by selecting the index of refraction of the material of the cladding sections 706A, 706B to be lower (e.g., about −0.04) than the index of refraction of the core section 708, a significant amount of light will be confined to the core section 708. If the same electrolyte is present in the core section 708 and the cladding sections 706A, 706B, then the index of refraction of the electrolyte within the cladding sections 706A, 706B is not the same as the index of refraction of the cladding material of sections 706A, 706B and light may be scattered within the cladding sections 706A, 706B. However, as described above, if the variation of index of refraction within the cladding sections 706A, 706B (or the core section 708) is substantially less than the wavelength of light being transmitted, then scattering of that light is reduced and the effective index of refraction of the combination of cladding sections 706A, 706B and the electrolyte will typically lie between the respective value of each of the two media but still be lower than the index of refraction of the core section 708.

In a different example in which the respective indices of refraction of the core section 708 and the electrolyte do not match, porous glass can be selected as the material for the core section 708 and the electrolyte can define the cladding sections 706A, 706B. Corning Vycor®, or controlled pore glass, can have pore size about 4 nm with a narrow distribution of sizes and relatively uniform pore spacing. If the index of refraction of this material is approximately 1.46, then such porous glass, when used as material for the core section 708, may effectively be transparent for 633 nm visible light even with a mismatch of the refractive index of the glass and that of the electrolyte, because the spatial variation in the index of refraction of the material (e.g., the pore spacing and pore sizes) is less than ½ the wavelength of such light. With that optical criteria met, the transmission of light through the core section 708 may be largely independent of the index of refraction of the electrolyte. Accordingly, a lower index of refraction than 1.46 can be selected for the electrolyte and the electrolyte can also serve as the cladding sections 706A, 706B. More specifically, the core section 708 can be constructed of porous glass with variation of its index of refraction less than ½ the wavelength of the light to be transmitted, and voids or spaces between the core section 708 and the electrodes can be filled with the electrolyte having an index of refraction less than that of the core section 708. The electrolyte will not only fill the pores of the core section 708 but will also form a layer of fluid acting as cladding sections 706A, 706B that are in contact with the core section 708 and the electrodes. Each cladding section 706A, 706B can be about 25 microns in thickness, for example. An example electrolyte, having an index of refraction of about 1.42 is EC/PC, a standard lithium-ion battery electrolyte.

Figure 7B:
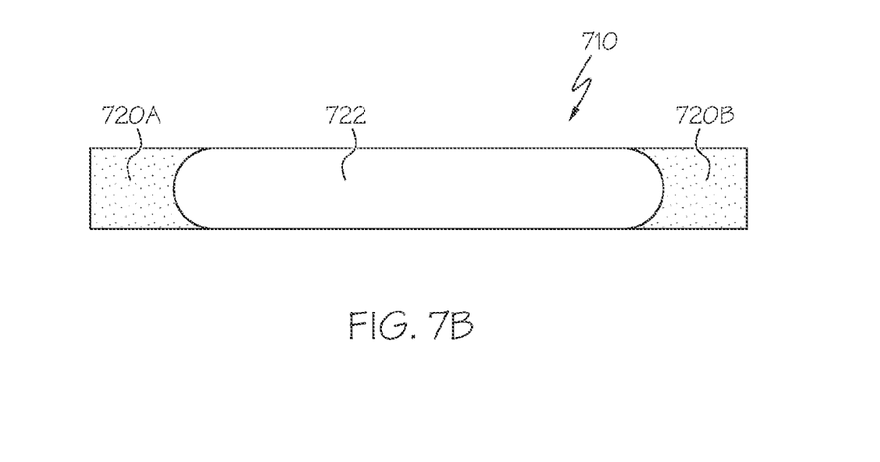
FIG. 7B schematically illustrates a view of the light transmitted out of the edge of the battery cell of FIG. 7A.

FIG. 7B illustrates a view of the light transmitted out of the edge 710 of the cell 700 that can be sensed by the light detector 704. The regions 720A and 720B correspond to the light that is transmitted out of the cladding sections 706A, 706B while region 722 corresponds to the light transmitted out of a central portion of the core section 708. The majority of light transmission occurs through this central region of core section 708 with typical values of light attenuation in the core section 708 around 0.1 to 10 dB/cm. The speckle pattern of FIG. 7B used for regions 720A, 720B is intended to indicate a reduced amount of light as compared to the region 722.

In another specific example, thin layers of glass can serve as cladding for core materials and electrolyte that have an index of refraction sufficiently greater than 1.46. For instance, the index of refraction of polypropylene is about 1.49 to about 1.51 so an electrolyte having a similar value, such as an ionic liquid, could be used with a polypropylene separator and a porous glass cladding providing the pore sizes and spacing for the glass are less than about ½ wavelength of the light to be transmitted (e.g., about 316 nm for visible light). Other porous materials such as ceramics, inorganics and polymers that also have appropriate pore characteristics could be used as well.

In general, the use of a material with small, uniform pore sizes, such that the spatial variation in the index of refraction is less than about 0.5 times the wavelength of light, enables any electrolyte that fills the pores to be used. Consequently, this porous material can serve as the core or serve as the cladding without matching the respective index of refraction of the other solid or the electrolyte. The electrolyte can then be selected to have an index of refraction to match the adjacent material (i.e., either the core or the cladding). As mentioned, porous material other than glass, such as ceramics, that have pore sizing and spacing that match the optical criteria can be used as well.

The above examples are provided merely as specific choices for materials that could be selected in accordance with the principles of the invention of the present application. The general principles described above are applicable in three different scenarios:
1. The index of refraction of the electrolyte can be substantially matched to the core section of the separator, but not matched to the cladding material around the core section. However, the cladding material can be selected to have pore sizes and uniformity of spacing that matches the optical criteria (i.e., less than about ½ the wavelength of the light to be transmitted.).
2. The index of refraction of the electrolyte can be matched to the cladding material, but not matched to the material of the core section of the separator. However, the core material can be selected to have pore sizes and uniformity of spacing that matches the optical criteria.
3. The index of refraction of the electrolyte may not be matched to either the cladding material or the core material, but both materials can be selected to have pore sizes and uniformity of spacing that match the optical criteria.

The above scenarios improve the amount of light transmitted through the core section 708 but it is still contemplated that the cell 700 of FIG. 7A can be constructed such that the indexes of refraction of either, or both, the core or cladding material do not match that of the electrolyte and both violate the optical criteria resulting in higher optical scattering losses than if the optical criteria was met. For example, the index of refraction of the electrolyte may be matched to that of the separator core, not matched to the cladding material and the cladding material may not meet the optical criteria. However, even though the light transmission may be lower than if the optical criteria was matched, the results sensed by the light detector 704 may still be acceptable.

One of the challenges in using an optical separator is the extraction of light from the separator so that methods for enhancing light extraction from the membrane are of interest. As seen in FIG. 6, scattering in the separator can result in light being widely distributed within the membrane. One method to enhance the amount of light that can be collected is to modify the membrane near the light emission edge to act as a lens. The refractive index of the light can be slightly modified to help funnel light toward the specific points on the edge where fibers will be connected. This refractive index modification can take place by various means, including thermal stress to slightly densify the polymer, chemical modification to increase or decrease the refractive index, or increased or decreased porosity imparted during manufacture. The change in refractive index in any of these methods can be controlled to channel the light exiting the separator toward a few discrete points, increasing the light collected by associated fibers.

An alternate or complementary approach to detecting the presence of dendrites or other faults is to measure the increase in light scattered at a sharp angle relative to an original light propagation direction. In a separator with high transmission such as described above, there may be relatively little light scattered at large angles, such as 90 degrees to the light propagation direction (or even 180 degrees to the light propagation direction). When a dendrite or other defect arises, the relative amount of light scattered into large angles may dramatically increase. Thus, the large relative increase in scattered light strength may be easier to detect than a relatively small decrease in transmission.

Figure 8:
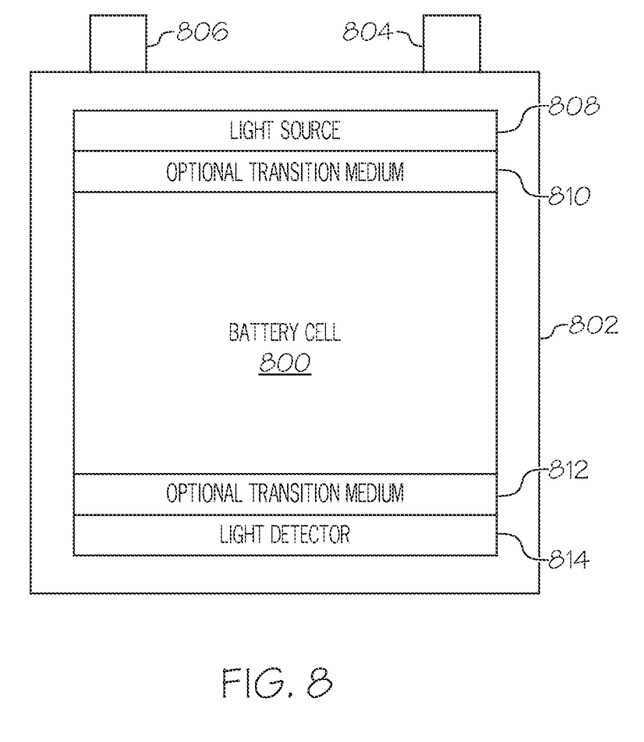
FIG. 8 illustrates a schematic view of a battery cell in accordance with the principles of the present application in which a light source, a light detector, or both can be located within a battery cell housing, or enclosure, along with the other typical components of a battery cell.

In at least some of the example battery cell and battery cell separators described above, the light source and light detector may have been located at an exterior of the battery cell with one or more optical fibers passing from the exterior to the interior and integrated into an edge of a battery cell separator. FIG. 8 illustrates a schematic view of a battery cell in accordance with the principles of the present application in which a light source, a light detector, or both can be located within a battery cell housing, or enclosure, along with the other typical components of a battery cell.

In FIG. 8, a battery cell housing 802 includes tabs 804, 806 which are connected with the electrodes of the battery cell and operate to pass current from an interior of the cell housing 802 to an exterior of the cell housing 802. Also within the cell housing 802 are a light source 808 and a light detector 814 arranged with respect to a battery cell 800. In FIG. 8, the light detector 814 and light source 808 happen to be arranged at opposite edges of the battery cell 800 such that light transmitted from the light source 808 into a battery cell separator is detected by the light detector 814. As described above, however, the light detector 814 does not have to be arranged at only this position but can be located at various positions with respect to the battery cell separator to detect transmitted, or scattered, light at various angles relative to a direction of propagation of the transmitted light.

The light source 808 may be directly coupled with an edge of the separator of the battery cell 800 such that the light source 808 essentially is in contact with the edge of the separator. Similarly, the light detector 814 can be directly coupled with the separator of the battery cell 800 as well. However, as shown in FIG. 8, an optional transition medium 810 can be located between the light source 808 and the battery cell 800 and another optional transition medium 812 can be located between the light detector 814 and the battery cell 800.

Typically, the light source 808 can be between about 0 and to 30 mm from the edge of the separator of the battery cell 800. The light source 808 may be coupled to the separator by focusing light from the source into the separator such as by a lens or other material. For example, based on the distance between the light source 808 and the edge of the separator of the battery cell 800, the light from the light source 808 could be caused to spread at an angle that increases an amount of light that enters the edge of the separator. The transition medium 810 can be a gel, liquid, solid, or gas, that is selected to have optical properties to transmit light from the light source 808 to the edge of the separator of the cell 800. For example, if the separator material is polyolefin with a refractive index of about 1.5, then one example suitable transition medium 810 would be acrylic also having an index of refraction of about 1.5. Matching the index of refraction reduces reflection at the interface of the two materials.

Typically, the light detector 814 can be between about 0 and 10 mm from an edge of the separator of the battery cell 800. As described in more detail below, the light detector may have a single sensing region or may include multiple pixels having discrete sensing regions. Thus, the optional transition medium 812 can be selected to direct light transmitted through the cell 800 to one or more areas of the light detector 814. The type of detector 814 utilized may have an effect on what types of materials are used in constructing the optional transition medium 812. In general, however, the refractive index of the optional transition medium 812 and that of the separator should be substantially matching in order to reduce reflection losses. This medium 812 can be a gel, liquid, gas or solid having appropriate optical properties. Although not shown in FIG. 8, the optional transition medium 812 can have cladding on one or more sides with an index of refraction selected to confine light within the medium 812.

Figure 9A:
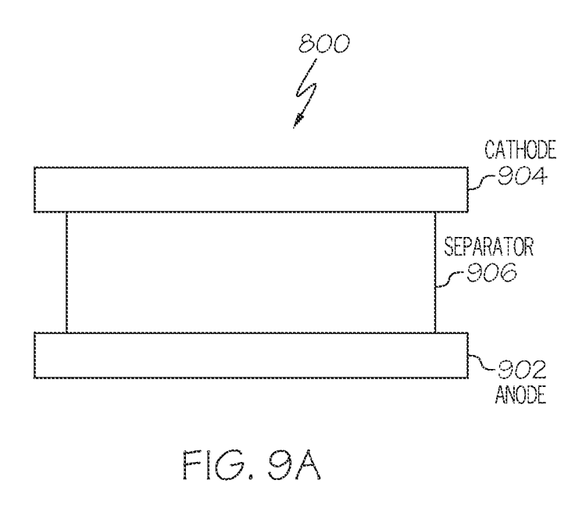
FIGS. 9A-9C illustrate schematically a top down view of three different arrangements of the battery cell of FIG. 8.
Figure 9B:
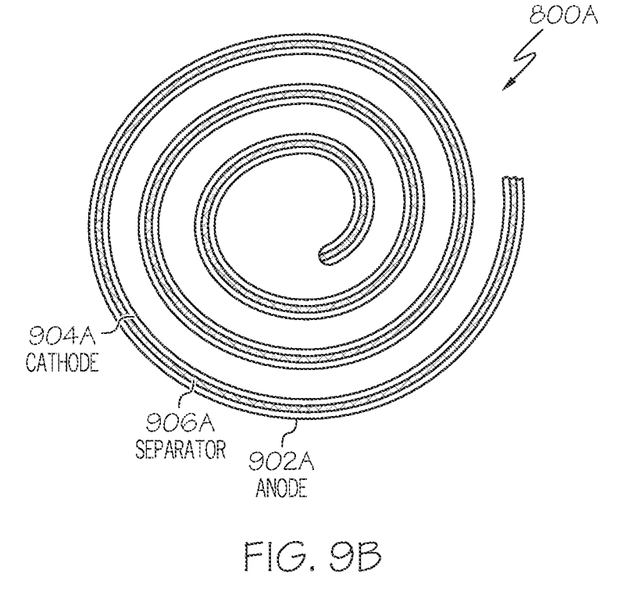

FIG. 9A illustrates a view looking down on a top of the battery cell 800 of FIG. 8. A planar cathode 904 and a planar anode 902 sandwich a planar separator 906. However, in many instances, the material of the cathode, anode and separator are flexible and the example structure of FIG. 9A may simply be conceptual in nature. In practice, a battery cell can be configured in a variety of different ways within the cell housing 802. In FIG. 9B, a battery cell 800A includes a cathode, 904A, a sandwiched separator 906A, and an anode 902A. However, these components are rolled so as to form multiple roll layers. Because, the light source 808 is located above the cell 800A, each of the different roll layers have one or more portions of their own respective edge of the separator 906A that can receive light from the light source 808. Similarly, on the opposite end of the cell 800B, each of the roll layers can have one or more portions of their own respective edge of the separator 906A that transmits light to the light detector 814.

Figure 9C:
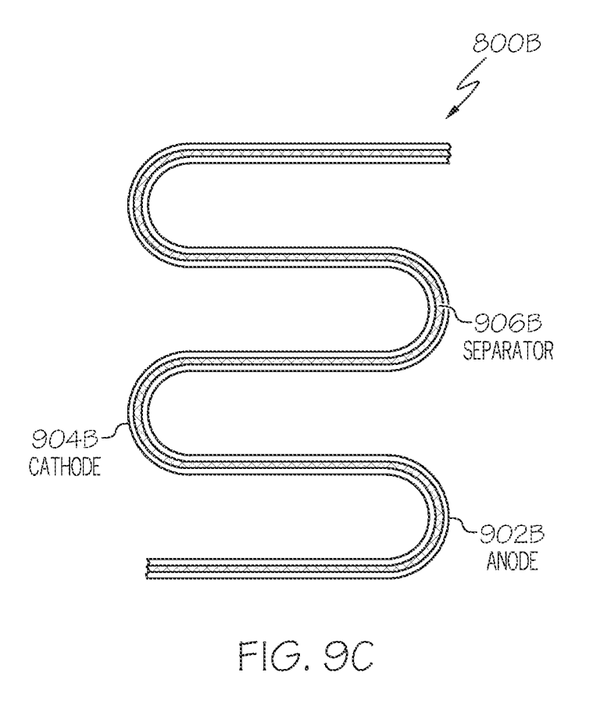

In FIG. 9C, the battery cell 800B also includes a cathode 904B, an anode 902B, and a separator 906B sandwiched between the two. However, in this arrangement, the cell 800B includes multiple folds wherein each fold has its own respective edge that can optically communicate with either the light detector 814 or the light source 808.

Figure 10:
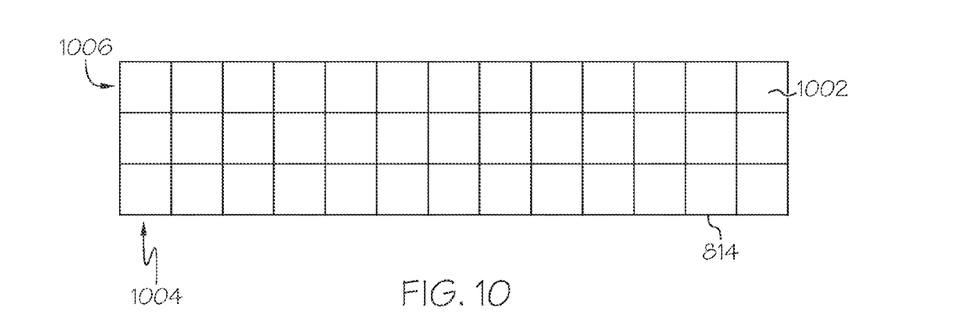
FIG. 10 illustrates one example light detector useful in conjunction with the battery cell of FIG. 8.

Based on the geometry of the battery cell 800, 800A, or 800B, the light source 808 can include multiple individual light sources and the light detector 814 can include multiple light sensors. For example, light detectors can be constructed from materials such as Silicon and InGaAs based on the wavelength of light they are to capture. One discrete light detector could be used with multiple light sources 808 that are arranged to transmit light to different portions of the separator of the battery cell. The individual light sources can be powered-on at different times so that the detected light at a particular time is related to one particular region of the separator. Alternatively, as shown in FIG. 10, the light detector 814 can be comprised of one or more rows 1006 and one or more columns 1004 so as to include a matrix of a plurality of pixels 1002 that each detects light exiting from a distinct region of the separator. The location of a pixel 1002 relative to the different portions of the separator would associate an output of that pixel 1002 with the impending fault condition at a particular region of the battery cell 800.

Figure 11:
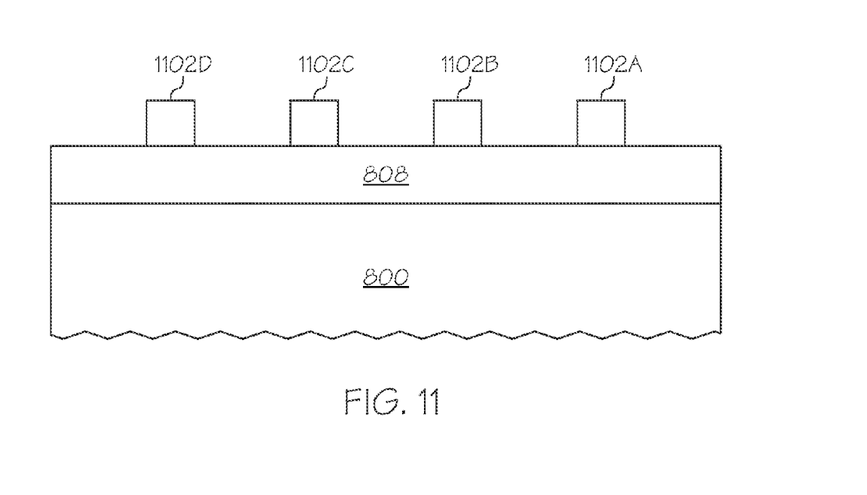
FIG. 11 illustrates one example light source useful in conjunction with the battery cell of FIG. 8.

FIG. 11 illustrates an example light source 808 that includes individual light-producing elements 1102A-1102D. The output from each of the elements 1102A and 1102D can be combined to effectively produce a single light source transmitting light to the edge of the separator as a whole, or they can be individually focused to transmit light to a selected region of the edge of the separator of the battery cell 800. The light source 808 can include various combinations of LEDs, lamps, lasers, OLEDs, and the like, while the light detector 814 can include solar cells, silicon photodetectors, LEDs, and similar devices.

The cell housing 802 of FIG. 8 can include one or more of the individual battery cells 800, 800A, and 800B shown in FIGS. 9A, 9B, and 9C, respectively. These plurality of cells can have their respective pair of electrodes connected in series or parallel to the tabs 804, 806 in order to produce a desired current and voltage at the exterior of the battery housing 802. Typical LEDs, OLEDs and other light source described above generally operate with voltages between about 1 to 10 volts. Also, circuitry to detect the light transmitted through the battery cell separator, provide signal conditioning and filtering and output that signal can be operated with voltages within that same range. Thus, sufficient voltage capacity exits within the battery housing 802 to drive the light source 808, the light detector 814, and ancillary support circuitry. Placing the light source 808, the light detector 814 and the ancillary circuitry within the cell housing, or enclosure, 802 will reduce the number of openings, or penetrations, between an interior of the housing 802 and an exterior.

Figure 12:
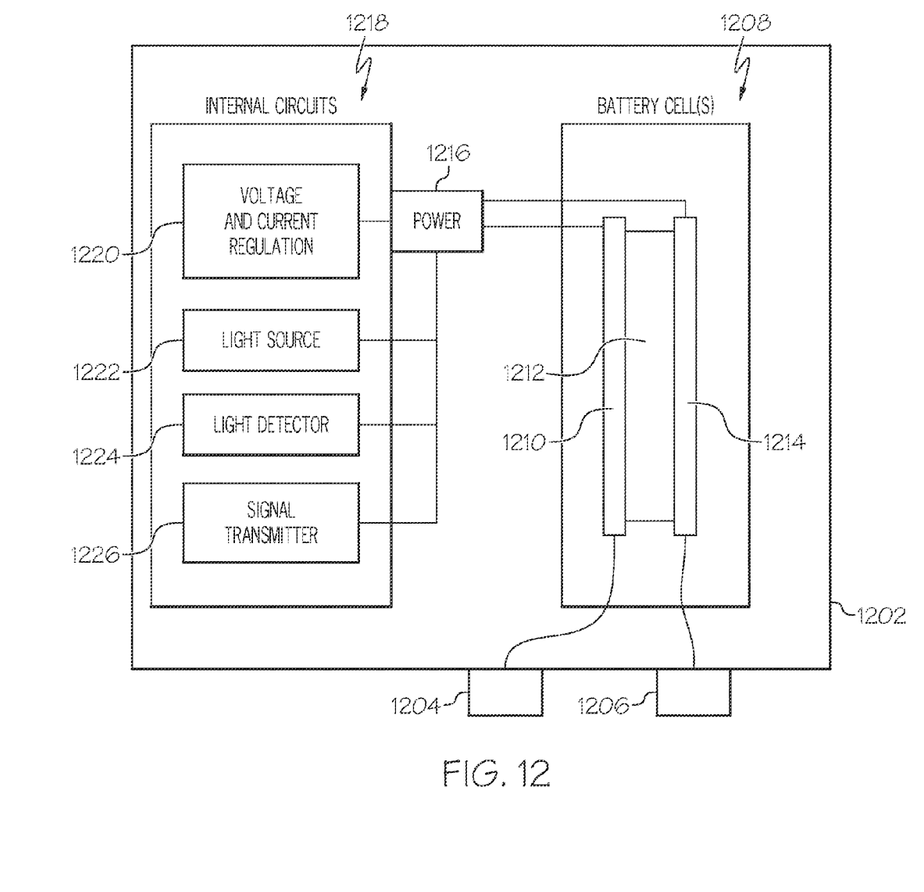
FIG. 12 illustrates schematically a battery housing that includes within its interior one or more battery cells and optical monitoring circuitry in accordance with the principles of the present application.

FIG. 12 illustrates schematically a battery housing that includes within its interior one or more battery cells and optical monitoring circuitry in accordance with the principles of the present application. One or more battery cells 1208 each have an anode 1210, a cathode 1214 and a separator 1212 that can transmit or scatter light as described above. The electrodes 1210, 1214 of the battery cell(s) 1208 are electrically connected with tabs 1204, 1206 to pass current from an interior of the housing 1202 to an exterior of the housing 1202. In addition, the electrodes of one or more of the cell(s) 1208 are connected with an input to a power distribution bus 1216 in order to provide power to a light source 1222 and a light detector 1224 so that these components may operate in a manner as that described in the numerous above examples.

The internal circuits 1218 can also include voltage and current regulation circuitry 1220 that generates appropriate voltages and currents for the circuits within the battery housing 1202. The regulator circuitry 1220 receives power from the battery cell electrodes and then provides power to the light detector 1224, the light source, 1222 and a signal transmitter 1226 through the power bus 1216.

The signal transmitter 1226 is coupled to the light detector 1224 and transmits an output signal indicative of the light received by the light detector 1224. As described above, a fault state of a portion of the battery cell 1208 associated with the light detector 1224 can be determined based on the received light. In one example, the signal transmitter 1226 can be connected to one or both of the tabs 1204, 1206 to communicate the output signal to the tab(s). For example, the signal transmitter 1226 can modulate the current passed by a cell tab to the exterior of the housing 1202. The signal transmitter 1226 can also include a wireless transmitter that outputs a wireless signal indicative of the light received by the light detector 1224.

In the above two examples, the output signal from the signal transmitter 1226 can be communicated with an exterior of the cell housing 1202 without any additional penetrations of the cell housing 1202. However, in some instances, the signal transmitter 1226 can be coupled to a signal wire, or pathway, that passes from the interior of the housing 1202 to an exterior pad or connection point. Control and monitoring equipment (not shown) external to the cell housing can collect and analyze the output signal(s) transmitted by the signal transmitter 1226. In this way, multiple batteries and multiple cells within multiple batteries can be centrally monitored for impending faults.

As mentioned, FIG. 12 provides a schematic view of an interior of the cell housing 1202. For example, in actual operation, the light source 1222 and light detector 1224 would be placed relative to the separator 1212 so that light could be transmitted through the separator 1212 for detection. The other circuitry of the internal circuits 1218, as well as the traces between the circuitry, can be located and routed based on available area and surfaces within the cell housing 1202. The circuitry could, for example, be conventional miniature electronics that are attached to various structures such as the sides of the housing 1202 or dedicated enclosures and circuit boards. Alternatively, one or more of the circuits 1220, 1220, 1224, 1226 can be fabricated with electronic components that can be printed or deposited on, or within, the separator 1212, for example.

Thus using chemical vapor deposition or a similar deposition or printing method, one or more of the electrically active components or conductive traces of the internal circuits 1218 can be printed on the separator 1212, the electrodes 1210, 1214, or some other surface within the cell housing 1202. Of course, a mixture of conventional electronic structures as well as flexible, or printed, components can be combined to achieve the functionality of the internal circuits 1218 illustrated in FIG. 12.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A battery structure for monitoring development of impending faults of a battery cell, the battery structure comprising:
   a cell housing;
   a battery cell comprising:
      a battery cell separator, located within the cell housing, formed of a light transmitting material that has light transmission characteristics that are a function of a state of an impending fault of the battery cell;
      a first electrode on a first side of the battery cell separator;
      a second electrode on a second side of the battery cell separator;
   a first cell tab connected to the first electrode and extending through and outwardly from the cell housing;
   a second cell tab connected to the second electrode and extending through and outwardly from the cell housing;
   a light source, located within the cell housing and external from an interior of the battery cell separator, positioned in optical communication with the battery cell separator to transmit light into said battery cell separator; and
   a light detector, located within the cell housing and positioned in optical communication with the battery cell separator to receive light transmitted through the battery cell separator,
   wherein an impending fault state of a portion of the battery cell associated with the light detector can be determined based on the received light, and
   wherein the cell housing encases the battery cell and is directly adjacent to the battery cell.

2. The battery structure of claim 1, comprising:
   a regulator circuit electrically coupled with the first and second electrodes and with the light source, configured to regulate at least one of a current or a voltage communicated to the light source.

3. The battery structure of claim 1, comprising:
   a transmitter coupled with the first and second electrodes and with the light detector, configured to transmit an output signal indicative of the light received by the light detector.

4. The battery structure of claim 3, wherein at least one cell tab of the first and second cell tabs is configured to pass current from an interior of the cell housing to an exterior of the cell housing, wherein the transmitter is electrically coupled with the at least one cell tab and communicates the output signal to the at least one cell tab.

5. The battery structure of claim 4, wherein the transmitter comprises:
   a modulator configured to modulate the current passed by the at least one cell tab based on the output signal.

6. The battery structure of claim 3, comprising:
   a signal wire having a first end located within an interior of the cell housing and a second, opposite end located at an exterior of the cell housing,
   wherein the first end is electrically coupled with the transmitter and communicates the output signal from the first end to the second end.

7. The battery structure of claim 1, comprising:
   a wireless transmitter coupled with the first and second electrodes and with the light detector, configured to transmit an output signal indicative of the light received by the light detector.

8. The battery structure of claim 1, wherein at least one of the light source and light detector comprises:
   flexible circuit traces deposited onto a portion of the battery cell separator.

9. The battery structure of claim 1, wherein the light detector senses a change in an amount of received light corresponding to at least one of light scattering or light absorption within the battery cell separator.

10. The battery structure of claim 1, wherein the light detector senses a change in an amount of IR energy.

11. The battery structure of claim 1, wherein the light source is in contact with the battery cell separator.

12. The battery structure of claim 1, wherein the first and second tabs extend through a common wall of the cell housing.

13. A method for monitoring development of impending faults of a battery cell in a battery structure, the battery structure comprising:
  a battery cell housing which encloses the battery cell, the battery cell comprising first and second electrodes on opposite sides of a battery cell separator, the battery cell separator formed of a light transmitting material that has light transmission characteristics that are a function of a state of an impending fault of the battery cell, wherein no other housing structure is positioned between the battery cell housing and the battery cell; and
  first and second cell tabs connected, respectively, with the first and second electrodes and each extending through and outwardly from the battery cell housing, the method comprising:
    transmitting, from a light source located within the battery cell housing and external from an interior of the battery cell separator, light into said battery cell separator;
    receiving, at a light detector located within the battery cell housing and in optical communication with the battery cell separator, light transmitted through the battery cell separator; and
    determining an impending fault state of a portion of the battery cell associated with the light detector based on the received light.

14. The method of claim 13, comprising:
regulating, using a regulator circuit electrically coupled with the first and second electrodes and with the light source, at least one of a current or a voltage communicated to the light source.

15. The method of claim 13, comprising:
electrically coupling a transmitter with the first and second electrodes and with the light detector; and
transmitting, from the transmitter, an output signal indicative of the light received by the light detector.

16. The method of claim 15, comprising:
electrically coupling the transmitter to at least one cell tab of the first and second cell tabs, the at least one cell tab configured to pass current from an interior of the cell housing to an exterior of the cell housing; and
transmitting the output signal to the at least one cell tab.

17. The method of claim 16, comprising:
modulating the current passed by the at least one cell tab based on the output signal.

18. The method of claim 15, comprising:
transmitting the output signal from a first end of a signal wire to a second end of the signal wire, wherein the first end is located within an interior of the cell housing and the second end is located at an exterior of the cell housing.

19. The method of claim 13, comprising:
coupling a wireless transmitter with the first and second electrodes and with the light detector; and
transmitting, using the wireless transmitter, an output signal indicative of the light received by the light detector.

20. The method of claim 13, wherein at least one of the light source and light detector comprises:
flexible circuit traces deposited onto a portion of the battery cell separator.

\* \* \* \* \*